United States Patent
Witzel et al.

[11] Patent Number: 5,347,033
[45] Date of Patent: Sep. 13, 1994

[54] PREPARATION OF 5-CYANOVALERAMIDE

[75] Inventors: Tom Witzel; Eberhard Fuchs, both of Ludwigshafen; Franz Merger, Frankenthal, all of Fed. Rep. of Germany

[73] Assignee: BASF Aktiengesellschaft, Ludwigshafen, Fed. Rep. of Germany

[21] Appl. No.: 82,585

[22] Filed: Jun. 28, 1993

[30] Foreign Application Priority Data

Jul. 1, 1992 [DE] Fed. Rep. of Germany ....... 4221604

[51] Int. Cl.$^5$ .................. C07C 253/30; C07C 255/29
[52] U.S. Cl. ...................................... 558/445; 558/459
[58] Field of Search ............................... 588/445, 459

[56] References Cited

U.S. PATENT DOCUMENTS

| | | | |
|---|---|---|---|
| 2,418,441 | 4/1947 | Whitman | 558/459 |
| 3,670,021 | 6/1972 | Goetz et al. | 260/561 |
| 3,928,439 | 12/1975 | Dockner et al. | 260/557 |
| 3,956,387 | 5/1976 | Dockner et al. | 260/561 |
| 3,980,662 | 9/1976 | Watanabe et al. | 260/295.5 |
| 4,176,137 | 11/1979 | Platz et al. | 260/561 |
| 4,386,018 | 5/1983 | Merger et al. | 568/862 |
| 5,151,543 | 9/1992 | Ziemecki | 558/459 |

FOREIGN PATENT DOCUMENTS

| | | |
|---|---|---|
| 0178106 | 4/1986 | European Pat. Off. . |
| 869052 | 3/1953 | Fed. Rep. of Germany . |

OTHER PUBLICATIONS

*J. Org. Chem.* vol. 15, (1950, pp. 800–801.
Chem. Ber., vol. 92, (1959), pp. 2616–2621.

*Primary Examiner*—Joseph Paul Brust
*Attorney, Agent, or Firm*—Keil & Weinkauf

[57] ABSTRACT

A process for preparing 5-cyanovaleramide by reacting adiponitrile with water at from 50° to 200° C. in the presence of a supported unionized-copper catalyst comprises employing from 1 to 15 mol of water per mole of adiponitrile and a residence time of from 5 to 60 minutes.

8 Claims, No Drawings

PREPARATION OF 5-CYANOVALERAMIDE

The present invention relates to a process for preparing 5-cyanovaleramide by reacting adiponitrile with water at from 50° to 200° C. in the presence of a supported unionized-copper catalyst.

The preparation of 5-cyanovaleramide from adiponitrile has been repeatedly attempted. J. org. Chem. 15 (1950), 800–801, describes obtaining 5-cyanovaleramide by hydrolysis in acetone solution with hydrogen peroxide in the presence of sodium hydroxide solution. Both the reaction and the workup are very complicated, and the yield is only 30%.

Chem. Ber. 92 (1959), 2616–2619, describes a process for preparing 5-cyanovaleramide by hydrolyzing adiponitrile with excess water (molar ratio 1:50) over a strongly basic ion exchanger. This process has the disadvantage that the catalyst deactivates rapidly through the formation of 5-cyanovaleric acid.

Furthermore, DE-A-2 429 269 discloses hydrolyzing adiponitrile with water at 100° C. over a copper catalyst in a polymer matrix of 4-vinylpyridine and divinylbenzene. The process has the disadvantage that long reaction times are necessary and that the 5-cyanovaleramide is only obtained in a yield of 5% while the troublesome adipamide is formed in a yield of 10%.

It is an object of the present invention to provide a process for preparing 5-cyanovaleramide from adiponitrile that gives improved yields, produces less adipamide as by-product, is simple to carry out, and employs a catalyst with a long life that is simple to regenerate.

We have found that this object is achieved by a process for preparing 5-cyanovaleramide by reacting adiponitrile with water at from 50° to 200° C. in the presence of a supported unionized-copper catalyst, which comprises employing from 1 to 15 mol of water per mole of adiponitrile and a residence time of from 5 to 60 minutes.

The novel process is remarkable in that, in the light of DE-A-2 320 060, it was unforeseeable that the hydration of adiponitrile in the presence of coppercontaining magnesium silicate catalysts would give 5-cyanovaleramide, since according to Example 4 of said DE-A only adipamide is obtained.

According to the invention, 1 mol of adiponitrile is reacted with from 1 to 15 mol of water, in particular from 2 to 11 mol of water.

The reaction is carried out at from 50° to 200° C. It is advantageous to maintain a temperature of from 70° to 150° C. Furthermore, the reaction is in general carried out under a pressure within the range from 100 to 300,000 kPa, in particular from 100 to 50,000 kPa. It is also preferable to ensure, by adapting the pressure and temperature conditions, that a liquid phase is present throughout the reaction.

The reaction is advantageously carried out in the presence of a water-soluble solvent that is inert under reaction conditions. Examples of suitable solvents are alkanols, in particular of from 1 to 3 carbon atoms, such as methanol, ethanol or propanol, also lactams such as pyrrolidone and caprolactam or $N$-$C_1$-$C_4$-alkyllactams such as N-methylpyrrolidone, N-methylcaprolactam or N-ethyl-caprolactam. Another example is tetrahydrofuran. In general, from 1 to 10 parts by weight of solvent are used per part by weight of adiponitrile.

According to the invention, the reaction is carried out in the presence of supported unionized-copper catalysts.

Suitable support/carrier materials are for example aluminum oxide, silicon dioxide, their mixed forms, magnesium silicates, aluminum silicates, zirconium dioxide and titanium dioxide.

A particular embodiment concerns magnesium silicate-supported unionized-copper catalysts. The unionized copper present in such catalysts is to an essential degree present from the start, for example in the form of freshly reduced copper added to the magnesium silicate prior to the treatment with reducing gases, or preferably forms copper compounds during the treatment. Advantageously, the copper comes from the copper compounds which are present during the precipitation of magnesium silicate and are converted by the reductive treatment into the unionized form. In addition to the bulk of unionized copper the treated catalyst may advantageously contain from 0.1 to 30, in particular from 0.1 to 10, % by weight, based on the total copper, of mono- and/or divalent copper, for example in the form of the original copper compound or in the form of a compound formed in the course of the treatment, such as copper silicate. In general, the total copper comprises from 25 to 70, in particular from 30 to 60, % by weight, based on the weight of the magnesium silicate contained in the catalyst.

Suitable copper compounds are for example the nitrate, sulfate, chloride, oxide, hydroxide, tartrate and acetate of monovalent or advantageously of divalent copper. The magnesium silicate is prepared in the presence of a copper compound that will deliver the unionized copper, by precipitating a magnesium compound together with an alkali metal silicate, advantageously a potassium or sodium silicate, in general in an aqueous precipitation medium, advantageously in a ratio of from 1 to 5 mol of alkali metal silicate per mole of magnesium compound. Suitable magnesium compounds are magnesium nitrate, sulfate, chloride, tartrate, acetate or oxalate. The precipitation is advantageously carried out at from 15° to 50° C. The copper compound may in part be present in the precipitation medium as a suspension.

The catalyst may contain small amounts of zinc, cadmium, chromium, molybdenum, tungsten, vanadium, titanium and/or thorium in the form of the metals or advantageously in the form of corresponding compounds. These additional metals advantageously comprise from 1 to 30, in particular from 1 to 10, % by weight, based on the weight of magnesium contained in the catalyst.

Suitable catalysts are obtained for example by precipitating a magnesium compound in an aqueous medium in the presence of copper compounds with or without one or more compounds of the additional metals by the process described in DR-C-869 052. Advantageously, the precipitated material, after washing and drying, is kneaded with an alkali metal silicate solution, for example a from 5 to 20% strength by weight sodium or potassium silicate solution, and after further drying at a slightly elevated temperature, for example at up to 30° C., formed. Preferably, 10–50% strength by weight aqueous solutions of the copper and magnesium compounds mentioned and 10–30% strength by weight aqueous solutions of alkali metal silicate are mixed with one another at the aforementioned precipitation temperature to form the precipitate over 1–60 minutes. The precipitate is then advantageously filtered off with suction, washed with water, for example until the removal has been effected of the original copper anion, such as the nitrate anion, then predried at 20°–30° C. formed for example into tablets, balls or strands, and then dried at 50°–70 °C.

The catalyst thus obtained is in general treated with a reducing gas under atmospheric or superatmospheric pressure in a continuous or batchwise manner at an elevated temperature, for example at from 100° to 230° C., preferably at from 180° to 230 °C. The gas used is in general hydrogen. The reduction time is advantageously from 1 to 15 hours. When prepared and dried the catalyst is advantageously first heated under nitrogen, preferably in a nitrogen stream, at for example 100°–180 °C., advantageously for 0.5–3 hours. This is followed by the reductive treatment, preferably over a period of from 0.5 to 24 hours, using in general from 5 to 15 mol of hydrogen per kilogram of catalyst. The preparation of suitable catalysts is described for example in DE-A-2 751 336, DE-A-2 320 060 and DE-A-2 320 061.

A further preferred embodiment concerns alumina-supported unionized-copper catalysts. Catalysts of this type are described in EP-A-44 444. Particular preference is given to carrying out the reductive treatment of these catalysts as per the process described in detail in DE-A-2 751 336.

The invention further stipulates carrying out the reaction with a residence time of from 5 to 60 minutes. A residence time of below 5 minutes generally gives too low a conversion, while a residence time of more than 60 minutes generally results in too low a selectivity.

The reaction can be carried out batchwise or preferably continuously. The reaction mixture is advantageously passed in liquid phase in a tube over a fixedbed catalyst while the specified reaction conditions are maintained. The 5-cyanovaleramide is simple to isolate from the resulting reaction mixture by extraction or in particular distillation.

The novel process has the advantage of minimizing the formation of adipamide. Another advantage is that the catalysts used have a long life and are easy to regenerate. A further advantage of the novel process is that it can be carried out continuously and produces yields which warrant industrial practice. 5-Cyanovaleramide is an important intermediate for caprolactam.

The process of the invention will now be exemplified.

EXAMPLE 1

A stainless steel reactor (length 1000 mm, diameter 10 mm) was equipped with a fixed bed of catalyst (60 g in the form of 1.5 mm strand extrudates) which contained 30% by weight of copper in the presence of magnesium silicates and had the composition specified in DE 2 751 336. The reductive treatment of the catalyst, likewise described in DE 2 751 336, was carried out directly in the reactor. After the reduction adiponitrile and water were passed upward through the catalyst for one hour.

The reaction parameters are listed in Table 1.

TABLE 1

| | Temp. [°C.] | ADN/H$_2$O [mol/mol] | ADN/Cat. [kg/kg*h] | RES [min] | SEL [%] | Yield [%] | CON [%] |
|---|---|---|---|---|---|---|---|
| a) | 100 | 1/10 | 7 | 5 | 72 | 19 | 26 |
| b) | 100 | 1/5 | 11 | 5 | 74 | 10 | 13 |
| c) | 100 | 1/1 | 20 | 5 | 100 | 1 | 1 |

ADN = adiponitrile; SEL = selectivity
RES = residence time; CON = conversion

The reactor exit mixture of Example 1a was concentrated and distilled to yield, per 100 g of exit mixture, 70 g of adiponitrile, 15 g of 5-cyanovaleramide (mp. 63°–65° C.; bp.$_{0.5}$ 148°–167° C.) and a residue of adipamide (5 g; mp. 224°–227 °C.).

EXAMPLE 2

In a glass flask 1 mol of adiponitrile and 5 mol of water were dissolved in 80 g of ethanol and admixed with 20 g of a 40% by weight copper catalyst in the presence of alumina and had the composition specified in Example 1 of EP-A-44 444. The reductive treatment of the catalyst was carried out at 100 kPa in a glass reactor as described in EP-A-44 444.

The suspension was heated at 90 °C. for 45 min. At that time 7% of the adiponitrile had been converted into 5-cyanovaleramide with a selectivity of 88%.

We claim:

1. A process for praparing 5-cyanovalerimide by reacting adiponitrile with water at from 50° and 200° C. in the presence of a supported copper catalyst wherein the sole catalytic agent comprises metallic copper and a support material, which comprises employing from 1 to 15 mol of water per mol of adiponitrile and a residence time of from 5 to 60 minutes.

2. A process as claimed in claim 1, wherein a temperature of from 70° to 150° C. is maintained.

3. A process as claimed in claim 1, wherein from 2 to 11 mol of water are employed per mole of adiponitrile.

4. A process as claimed in claim 1, wherein the support materials of the supported copper catalyst used are selected from the group consisting of aluminum silicate, magnesium silicate, aluminum oxide, silicon dioxide, titanium dioxide, and zirconium dioxide.

5. A process as claimed in claim 1, wherein the catalyst contains from 1 to 30% by weight of at least one element selected from the group consisting of zinc, cadmium, chromium, molybdenum, tungsten, vanadium, titanium and thorium, or compounds thereof.

6. A process as claimed in claim 1, wherein a water-miscible solvent that is inert under reaction conditions is present.

7. A process as claimed in claim 1, wherein an alkanol of from 1 to 3 carbon atoms is present as solvent.

8. A process as claimed in claim 1, wherein at least 5 mol of water are employed per mole of adiponitrile and a yield of at least 10% of 5-cyanovaleramide is obtained.

* * * * *